United States Patent [19]

Dozier, Jr.

[11] Patent Number: 4,815,454
[45] Date of Patent: Mar. 28, 1989

[54] APPARATUS AND METHOD FOR INJECTING BONE CEMENT

[76] Inventor: John K. Dozier, Jr., #8 Stonegate, Houston, Tex. 77024

[21] Appl. No.: 121,086

[22] Filed: Nov. 16, 1987

[51] Int. Cl.[4] .............................................. A61F 5/04
[52] U.S. Cl. .............................................. 128/92 VQ
[58] Field of Search ................. 128/92 VP, 234, 256, 128/242, 342, 344, 658, 92 VQ; 604/15-18, 57, 61, 82, 88, 92, 218, 222, 104, 174, 278; 623/16, 17; 222/43, 74, 213, 225

[56] References Cited

U.S. PATENT DOCUMENTS

| | | | |
|---|---|---|---|
| 3,721,229 | 3/1973 | Panzer | 128/343 |
| 4,338,925 | 7/1982 | Miller | 128/92 VQ |
| 4,488,549 | 12/1984 | Lee et al. | 128/92 VP |
| 4,595,006 | 6/1986 | Burke et al. | 128/92 VQ |

*Primary Examiner*—Robert A. Hafer
*Assistant Examiner*—Charles H. Sam
*Attorney, Agent, or Firm*—Kenneth A. Roddy

[57] ABSTRACT

A sealing plug and expander is used in the operation known as total hip replacement wherein the head of the femur bone is removed leaving an opening and replaced with prosthetic components fixed into the bone cavity with penetrating cement. An expansible, elastomeric pressure sealing plug has a generally rectangular portion, a peripheral flange surrounding the rectangular portion at one end, and a central longitudinal hole therethrough which receives a rigid wedge-shaped expander member. The expander has a central inwardly tapered bore which frictionally receives the tubular nozzle of a bone cement cartridge when the nozzle is pressed therein to form a pressure sealing relation therewith. In the relaxed condition, the sealing plug rectangular portion is frictionally received within the femoral canal opening and the flange surrounds the exterior bone surface around the opening of the femoral cavity. The expander member is inserted into the hole in the sealing plug whereby the side walls of the sealing plug are forced radially outward to seal the opening of the femoral cavity. In the expanded condition, the expander and sealing plug provide a pressure seal between the bone cavity opening and the injection gun whereby the penetrating bone cement will be injected into the bone cavity under substantially pressure and will penetrate between the trabeculae of the bone to thereby provide a bone/cement interface to securely hold the prosthetic device in place.

9 Claims, 1 Drawing Sheet

U.S. Patent   Mar. 28, 1989   4,815,454
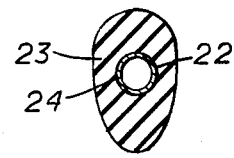
FIG. 2
(PRIOR ART)
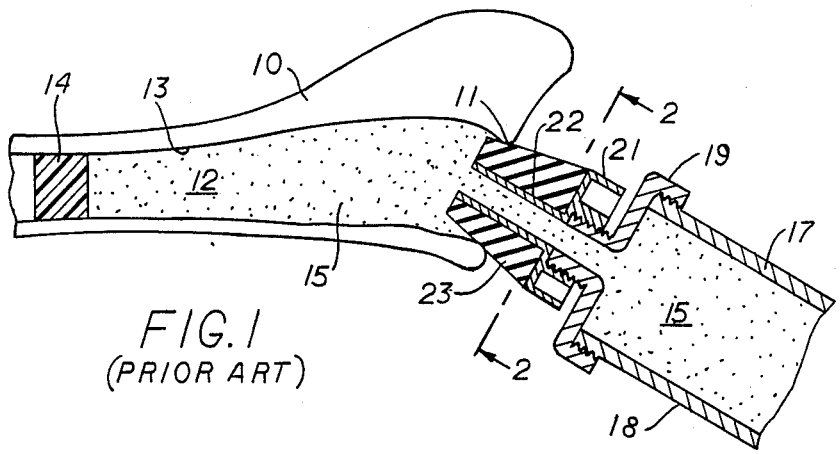
FIG. 1
(PRIOR ART)
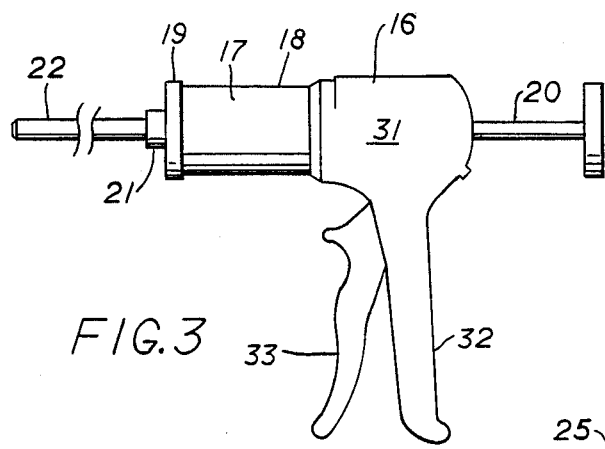
FIG. 3
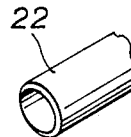
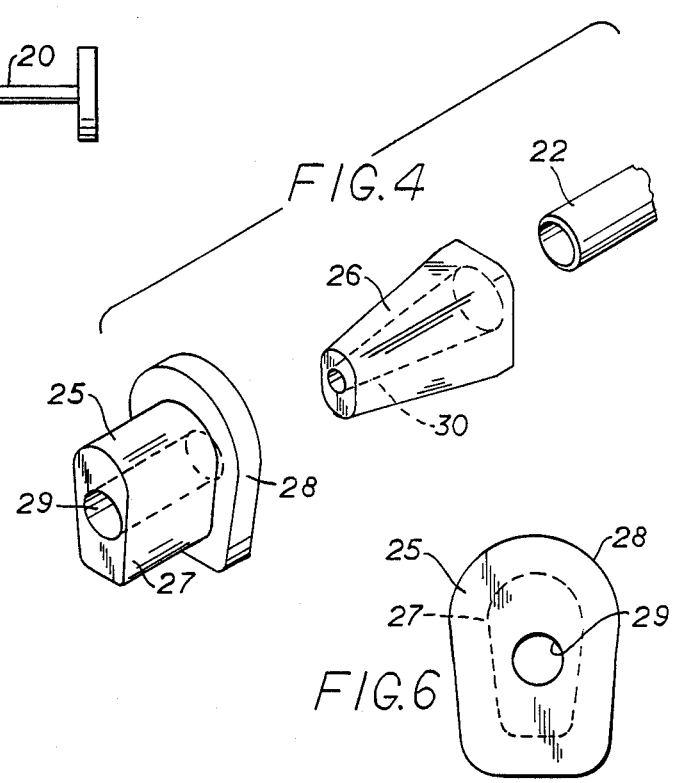
FIG. 4
FIG. 6
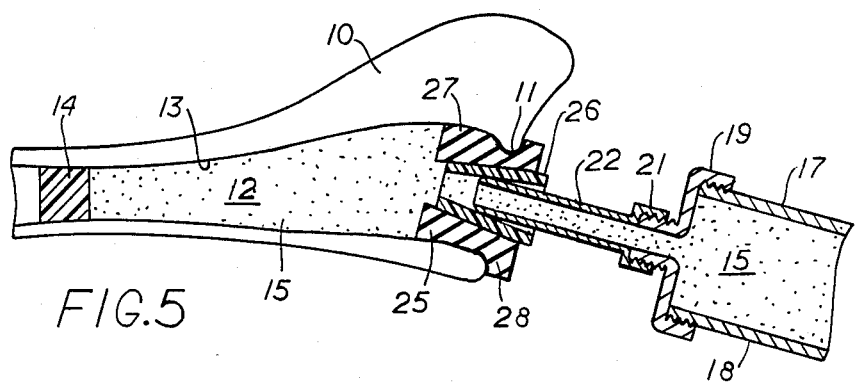
FIG. 5
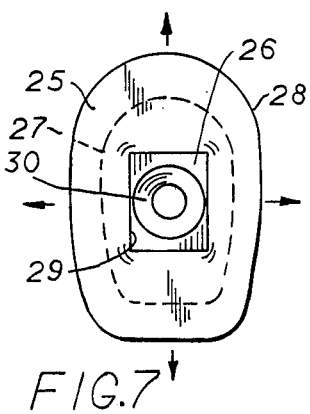
FIG. 7

APPARATUS AND METHOD FOR INJECTING BONE CEMENT

BACKGROUND OF THE INVENTION

1. Field of the Invention

The invention generally relates to improved fixation of a prosthetic component to bone and, in particular, relates to an apparatus for and method of pressure injection of low viscosity bone cement into bone surfaces to improve the bone/cement interface.

2. Brief Description of the Prior Art

Total arthroplasty, or total hip replacement, is a widely accepted Orthopaedic operation used in the correction of damaged or diseased bones, and the treatment of severe arthritis. A portion of the bone is removed and replaced with suitable metal and plastic components fixed into the bone with cement. The operation facilitates the correction of deformity, the reestablishment of stability, and the relief of pain. Occasionally complications associated with the procedure arise, such as loosening of the arthroplasty components. A number of factors contribute to loosening including failure to correct a deformity, an overweight or overactive patient, an osteoarthritic joint in comparison to a rheumatoid joint and the use of a constrained prosthesis. The consequences of loosening include return of pain and deformity, the need for further reconstructive surgery with attendant technical difficulties and increased risk of sepsis and possible risk of subsequent reloosening. Failure of the fixation often originates at the interface between the prosthesis and cement, at the interface between the cement and bone or both.

Loosening of the joint arthroplasty components occurs in a number of ways. Resorption of the bone commonly occurs particularly, around the stem of a constrained prosthesis and is the result of high loads placed on the cement/bone interface leading to micromovement, resorption and gross loosening. Separation of the cement from the bone is usually due to a weak bone/cement interface and results in gross displacement of the implant. A radiolucent line is commonly seen between the cement and bone and has the following characteristics. Microscopic examination of the interface between the cement and bone indicates that the radiolucent line corresponds to a fibrous membrane which has developed at the interface. Mechanically, the fibrous membrane presents a plane of weakness between the cement and bone and a potential site for loosening. Micromovement occurs at those interfaces where a fibrous membrane is interposed. The radiolucent line, therefore, represents a site of impaired mechanical integrity.

Failure of the cement/bone interface may be due to a mechanically incompetent interface from the moment of implantation. Often, doughy cement having a viscosity at 68° to 70° F. of greater than 4000 poise at the 5th or 6th minute after mixing is applied to cancellous surfaces by hand and penetrates trabeculae in the bone only to limited degree, if at all. More practically it may conform to surface irregularities, but does not penetrate the bone. Poor fixation of this type leads to micromovement which in turn leads to bone resorption which results in the development of a fibrous membrane. Acrylic cements as currently used for the fixation of joint arthroplasty components to bone has inherent deficiencies in terms of establishing secure and enduring interfaces between the prosthesis and the cement and between the cement and the bone.

Bone cement is viscoelastic in its early stages. As it cures it becomes hard and in the hardened state, fastens the components in place. Several factors enhance penetration of the bone cement into bone such as; viscosity of the cement, cleanliness of the bone, and pressure applied to the cement. These factors interplay to achieve penetration of the cement in the bone. The present invention seeks to decrease the possibility of cement loosening by better pressurization during application.

There are several patents which disclose apparatus and methods for injection of bone cement and other materials.

Miller, U.S. Pat. No. 4,338,925 is directed primarily to a cement gun and pressure injection method employing a variety of tips for the cement injection gun including a femoral canal pressurizer plug and adapter. The adapter nozzle is formed of polyethylene and screws onto the end of the cement cartridge and has a tubular extension. The pressurizer is a tapered silicone rubber plug having a generally oval cross section with a central longitudinal hole therethrough to slidably receive the tubular extension. The pressurizer plug fits onto the adapter at the end of the gun to seal the proximal end of the femur after the medullary canal has been filled. Although the plugs may be furnished in a variety of sizes, the Miller device does not provide a consistently reliable seal due to the irregular shape and range of sizes of the prepared opening of the bone cavity. The tubular extension inside the hole does not provide lateral expansion of the sealing member, and in use, leakage of pressure and cement occurs.

Malcom et al, U.S. Pat. No. 4,274,163 discloses an artificial prosthesis having opening which is clamped in place over the opening of the bone to which is being secured and cement is applied through the prosthesis under pressure. The rim of the prosthesis may be provided with an O-ring seal or deformable gasket to seal against the matching bone surfaces.

Panzer, U.S. Pat. No. 3,721,229 discloses an obturator device for the injection of fluid into a body cavity through a narrow passageway. The device comprises an injection tube reciprocally movable through an obturating collar and secured thereto by an elastic sleeve of intermediate enlarged diameter disposed around the tube. The sleeve is distended to reduced diameter for movement of the tube through the passageway and, on release, to return to its natural expanded diameter to lock the tube to the passageway wall.

The present invention is distinguished over the prior art in general, and these patents in particular by an expansible, elastomeric pressure sealing plug having a generally rectangular portion, a peripheral flange surrounding the rectangular portion at one end, and a central longitudinal hole therethrough which receives a rigid wedge-shaped expander member. The expander has a central inwardly tapered bore which frictionally receives the tubular nozzle of a bone cement cartridge when the nozzle is pressed therein to form a pressure sealing relation therewith. In the relaxed condition, the sealing plug rectangular portion is frictionally received within the femoral canal opening and the flange surrounds the exterior bone surface around the opening of the femoral cavity. The expander member is inserted into the hole in the sealing plug whereby the side walls of the sealing plug are forced radially outward to seal the opening of the femoral cavity. In the expanded condition, the expander and sealing plug provide a pressure seal between the bone cavity opening and the injection gun whereby the penetrating bone cement will be injected into the bone cavity under substantial pressure and will penetrate between the trabeculae of the bone to thereby provide a bone/cement interface to securely hold the prosthetic device in place.

SUMMARY OF THE INVENTION

It is therefore an object of this invention to provide a cement injecting apparatus which seals a bone cavity at high pressure resulting in effective penetration of bone cement in the trabeculae.

It is another object of this invention to provide a method for pressurizing a bone cavity with penetrating bone cement to receive a prosthetic component.

It is another object of this invention to provide a novel seal apparatus which may be used with conventional cement injection guns and applicators.

It is another object of this invention to provide a novel seal apparatus which expands to conform to the shape of an irregular bone opening to forming a sealing engagement.

It is another object of this invention to provide a novel seal apparatus which expands to seal against the inside walls of a bone cavity adjacent.

It is another object of this invention to provide a novel seal apparatus having a peripheral flange to sealingly engage the exterior plateau surface surrounding the opening of a bone.

It is a further object of this invention to provide an apparatus for injecting bone cement which is simple in design, economical to manufacture, durable in use, and reliable in operation.

Other objects of the invention will become apparent from time to time throughout the specification and claims as hereinafter related.

The above noted objects and other objects of the invention are accomplished by an expansible, elastomeric pressure sealing plug having a generally rectangular portion, a peripheral flange surrounding the rectangular portion at one end, and a central longitudinal hole therethrough which receives a rigid wedge-shaped expander member. The expander has a central inwardly tapered bore which frictionally receives the tubular nozzle of a bone cement cartridge when the nozzle is pressed therein to form a pressure sealing relation therewith. In the relaxed condition, the sealing plug rectangular portion is frictionally received within the femoral canal opening and the flange surrounds the exterior bone surface around the opening of the femoral cavity. The expander member is inserted into the hole in the sealing plug whereby the side walls of the sealing plug are forced radially outward to seal the opening of the femoral cavity. In the expanded condition, the expander and sealing plug provide a pressure seal between the bone cavity opening and the injection gun whereby the penetrating bone cement will be injected into the bone cavity under substantial pressure and will penetrate between the trabeculae of the bone to thereby provide a bone/cement interface to securely hold the prosthetic device in place.

BRIEF DESCRIPTION OF THE DRAWINGS

FIG. 1 is a sectional view of a prior art pressure injection apparatus and sealing member used to pressurize the bone cement in the femoral canal; and FIG. 2 is a sectional view taken along lines 2—2 of FIG. 1 showing the seal member of the prior art apparatus.

FIG. 3 is an elevation view of an injection gun and cartridge to be used with the present invention;

FIG. 4 is an exploded isometric view of the components of the present invention in an unassembled condition;

FIG. 5 is a sectional view of the improved pressure injection apparatus and sealing members according to the present invention used to pressurize the bone cement in the femoral canal;

FIG. 6 is a top plan view of the expansible seal member in the relaxed condition prior to having the wedge expander member installed therein; and FIG. 7 is a sectional view taken along lines 7—7 of FIG. 5 illustrating the expansible seal member in the expanded condition after having the wedge expander member installed therein.

DESCRIPTION OF THE PREFERRED EMBODIMENT

In order to achieve effective pressurization of penetrating cement into the trabeculae of the bone, it is essential to have a cavity which can be closed off to create a closed space. Although suitable for other bone surfaces, the present invention is particularly suited for a long tubular canal such as that in the long bone of the femur for a hip replacement.

In the operation of total hip replacement, the head of the femur (thigh bone) is removed leaving an irregular shaped, generally oval opening at the top end of the bone and the interior of the bone is reamed so that the surgeon creates a situation analogous to an open vase. To create a closed space for preventing the extension of bone cement beyond the point where it is useful, and to facilitate more complete filling and pressurization of the cavity, the lower end of the reamed area is plugged by various means. Various means of plugging the cavity are used, including plugs made of natural bone, polyethylene or a bolus of doughy bone cement. The plugged femur is then filled with cement from the plug upward to the very lip of the opening of the femur. To obtain pressurization of the cement and the femur, it is very important to occlude the open end of the femur in a very tight manner similar to a tightly sealed bottle.

Referring now to the drawings by numerals of reference, there is shown in FIGS. 1 and 2, a prior art pressure injection apparatus and sealing member used to pressurize the bone cement 10 in the femoral canal 12. FIG. 3 shows a typical cartridge type cement injection gun 16 which is used with the present invention. Common cement cartridges 17 contain a penetrating bone cement 15 held within a cylinder 18 having a flange 19 at one end and a plunger 20 at the other end. A front closure cap 21 allows for front loading of the cement into the cartridge and also for the interchangeability of tips or nozzles 22.

In the prior art, a tubular nozzle 22, usually formed of polyethylene, is screwed onto the end of a cement cartridge 17. A rubber pressurizer plug 23 having a generally oval cross section and a central longitudinal hole 34 therethrough is slidably received on the tubular nozzle 22. The exterior of the pressurizer plug 23 is tapered inwardly at the front end to terminate in a portion having a diameter less than the diameter of the bone cavity 12. This allows the tapered portion of the plug 23 to be inserted into the bone cavity. In theory, the exterior of the rubber pressurizer plug 23 supposedly fits into the opening 11 to seal the proximal end of the femur 10. In an actual surgical setting, the cut end of the bone is slightly irregular and since it is a biological entity, no two specimens are exactly the same shape and size.

Although the plugs 23 may be furnished in a variety of sizes, the prior art apparatus does not provide a consistently reliable seal due to the irregular shape and range of sizes of the bone cavity opening 11. The surgeon must select the most appropriate size plug available, and manually effect a seal by pressing the seal into the femur opening while at the same time operating the injection gun. Often the plug will slip out of position or the pressure will be relaxed. The tubular nozzle 22 inside the hole 24 does not provide lateral expansion of the sealing member, and in use, leakage of pressure and cement occurs.

As shown in FIGS. 4–7, the present invention overcomes this problem by providing an expansible seal at the opening which conforms to the opening configuration and seals against the interior side walls of the cavity during pressurization.

The present apparatus comprises an expansible sealing plug 25 and a rigid wedge-shaped expander member 26. The sealing plug 25 has a generally rectangular main body portion 27 with a peripheral flange 28 extending radially outward therefrom at one end. A central longitudinal bore 29 extends through the plug 25. The plug 25 has a generally T-shaped longitudinal cross section and a generally rectangular transverse cross section tapered inwardly at one end. The exterior of the main body 27 has rounded corners and is dimensioned to frictionally fit into the opening 11 of the femur 10 with the flange portion 28 engaging the plateau surface surrounding the opening. The sealing plugs 25 may be furnished in a variety of sizes to fit a range of opening configurations. The plug 25 is formed of a suitable elastomer, such as silicone rubber. Silastic (TM Dow Corning Corp.) has proven to be a suitable material having the desired elasticity and resilience qualities. Dow Corning Elastomer MDX4-4210 in combination with Dow-Corning Fluid #360 has been found to produce a satisfactory material.

The wedge-shaped expander member 26 is a generally rectangular configuration formed of rigid plastic material tapered inwardly at one end and having a generally rectangular cross section. A tapered longitudinal bore 30 extends through the expander member 26 and tapers inwardly through its length. The inwardly tapered exterior end of the expander member 26 is slightly greater than the diameter of the bore 29 of the plug 25. To install the expander 26 into the plug 25 after the plug is placed in the opening 11, a suitable lubricating jelly is applied to the expander exterior surface and the tapered end of the expander is pressed into the bore 29, thus expanding the plug 25 radially.

The plug 25 expands to conform to the shape of the opening forming a sealing engagement therewith, the lower portion 27 of the plug expands to seal against the inside walls of the cavity 12 adjacent the opening, and the flange 28 sealingly engages the exterior plateau surface surrounding the opening. Thus, the opening of the femur is tightly occluded. The tapered bore 30 of the expander 26 receives the end of a tubular nozzle 22 attached to the cement cartridge 17 carried by the injection gun 16. Because the bore 30 is tapered, the adapter 26 will receive and frictionally engage a wide range of conventional nozzle diameters when pressed into the bore. Pressure is then produced within the cement mass by means of the cement injection gun (similar to a caulking gun), which is inserted into the tapered bore of the expander.

OPERATION

While the operation of this apparatus should be apparent from the foregoing description of its construction and assembly, a further description will be given to facilitate a thorough understanding of the improved method of pressure injecting bone cement.

In the operation of total hip replacement, the head of the femur (thigh bone) 10 is removed leaving an irregular shaped, generally oval opening 11 at the top end of the bone and the interior of the bone is reamed so that the surgeon creates a situation analogous to an open vase. To create a closed space for preventing the extension of bone cement beyond the point where it is useful, and to facilitate more complete filling and pressurization of the cavity, the lower end of the reamed area 13 is plugged by various means, such as installing a plug 14 of natural bone, polyethylene, or a bolus of doughy bone cement. The plugged femur 10 is then filled with penetrating bone cement 15 from the plug 14 to the very lip of the opening 11 of the femur.

As used herein, the term "penetrating bone cement" connotes a bone cement which is capable of penetrating the trabeculae of bones when applied thereagainst under substantial pressure during its period of workability. A suitable penetrating cement presently known is an acrylic cement having a low viscosity of less than 2000 poise, at 68° to 70° F. during a working period of up to 5 to 6 minutes after mixing.

The injection gun 16 for extruding the bone cement from the cement cartridge 17 is similar to a "caulking gun" having a housing 31 with a handle 32 and trigger 33.

Initially, a conventional long straight tip or nozzle which has a diameter less than the diameter of the cavity 12 to allow the tip to project into the bone cavity is installed on the end of the cement cartridge 17 and used to deposit bone cement 15 into the long bone cavity 12. The surgeon performing the fixation grasps the handle 32 and trigger 33 of the gun 16 and squeezes them together. This causes the injection gun to develop high pressure while applying bone cement to the bone canal. Common injection guns will extrude anywhere from 2 or 3 to 10 or 15 cubic cm of cement with a single actuation of the trigger.

After the cavity 12 has been filled up to the lip of the opening 11, the apparatus of the present invention, as shown in FIGS. 4–7, is used to complete the filling of the cavity and pressurize the contents of the cavity to force the cement to penetrate the bone.

The expansible sealing plug 25 is then pushed into the opening 11 with the main body portion 27 inside the cavity 12 and the peripheral flange 28 engaging the plateau surface on the outside of the opening. The exterior surface of the wedge-shaped expander member 26 is coated with a lubricating jelly and the tapered end of the expander is pressed into the hole 29 of the plug 25, thus expanding the sealing plug radially.

The plug 25 expands to conform to the shape of the opening 11 forming a sealing engagement, the lower portion 27 of the plug expands to seal against the inside walls of the cavity 12 adjacent the opening 11 and the flange 28 sealingly engages the exterior plateau surface surrounding the opening. Thus, the opening of the femur is tightly occluded.

The tubular tip or nozzle 22 of the cement cartridge 17 is pushed into the tapered bore 30 of the expander member 26 and becomes frictionally engaged on the bore side wall. Pressure is then produced within the cement mass by pressing the cement injection gun 16 against the assembled seal 25 and expander 26 and squeezing the handle 32 and trigger 33 of the gun together. This causes the injection gun to develop high pressure within the cement mass.

The expansible sealing plug 25 in the expanded condition provides a pressure seal between the bone cavity opening 11 and the injection gun whereby the penetrating bone cement 15 will be injected into the bone cavity 12 under substantial pressure and will penetrate between the trabeculae of the bone to thereby provide a bone/cement interface to securely hold said prosthetic device in place.

Results of laboratory tests measured by a pressure transducer has shown that the present invention installed in bone replicas and actual cadaver specimens will produce from 300 to 550 kpa with a typical pressure of from 500–550 kpa within the cement mass over a several second span of time. Pressures have typically ranged from 500–550 kpa.

Similar pressures can be obtained with existing prior art devices as described herein, however there is frequently a problem of sudden loss of pressure due to leakage of cement from the open mouth of the femur with the prior art devices because of the inconsistent plugging effect at the irregular opening at the mouth of the femur. The present plug, which expands to fit the opening of the femur, more consistently provides leak resistance and allows the required pressure to build to force the cement to penetrate the trabeculae of the bone.

Following a short period of cement pressurization, the stem of the prosthesis is inserted into the cement and the cement is allowed to harden.

While this invention has been described fully and completely with special emphasis upon a preferred embodiment, it should be understood that within the scope of the appended claims the invention may be practiced otherwise than as specifically described herein.

I claim:

1. Apparatus for sealing the opening of a bone cavity during injection of penetrating bone cement into the bone cavity under sufficient pressure to cause the cement to penetrate between the trabeculae of the bone prior to placement of a prosthetic device into the bone cavity, said apparatus comprising;

expansible pressure sealing means configured to be frictionally and removably received partially within a bone cavity opening in a relaxed condition and having a central aperture extending therethrough, and expander means frictionally received within the central aperture of said sealing means and configured to expand said sealing means radially outward to engage and form a seal in the bone cavity opening in the expanded condition, said expander means having a passageway in communication with the bone cavity to receive and sealingly engage the tubular nozzle of a bone cement injecting means and conduct cement extruded therefrom into the bone cavity, said expander means and said pressure sealing means in the expanded condition providing a pressure seal between the bone cavity opening and the injecting means whereby the penetrating bone cement will be injected into the bone cavity under substantial pressure and will penetrate between the trabeculae of the bone to thereby provide a bone/cement interface to securely hold said prosthetic device in place.

2. Apparatus for sealing the opening of a bone cavity according to claim 1 in which said expansible sealing means comprises a generally rectangular member formed of elastomeric material and configured to fit within a femoral canal and provide a pressure seal within the opening of a femoral cavity in an expanded condition.

3. Apparatus for sealing the opening of a bone cavity according to claim 1 in which said expansible sealing means comprises a generally rectangular member formed of elastomeric material and having a generally rectangular portion configured to fit partially within a femoral canal for providing a pressure seal within the opening of a femoral cavity in an expanded condition, and a peripheral flanged portion surrounding the rectangular portion at one end thereof to sealingly engage the exterior plateau surface surrounding the opening of the femoral cavity.

4. Apparatus for sealing a bone opening according to claim 1 in which said expansible sealing means comprises a generally rectangular member formed of elastomeric material and configured to fit within a femoral canal and provide a pressure seal within the opening of a femoral cavity in an expanded condition and having a central longitudinal aperture extending therethrough, and said expander means comprises a tapered member formed of rigid material and configured to be frictionally received within the central longitudinal aperture of said sealing means, said expander means tapered inwardly from one end to the other whereby the side walls of said sealing means will be forced radially outward to seal the opening of the femoral cavity as said expander means is pressed into said sealing means longitudinal aperture.

5. Apparatus for sealing the opening of a bone cavity according to claim 4 in which said expansible sealing means having a peripheral flanged portion surrounding the rectangular portion at one end thereof to sealingly engage the exterior plateau surface surrounding the opening of the femoral cavity.

6. Apparatus for sealing the opening of a bone cavity according to claim 4 in which said expander means having a central longitudinal bore tapered inwardly from one end to the other whereby the side wall of the tubular nozzle of the cement injection means will frictionally engage the tapered bore when said nozzle is pressed therein to form a pressure sealing relation therewith.

7. Apparatus for sealing the opening of a bone cavity according to claim 4 in which said expander means comprises a generally rectangular wedge-shaped member having tapered side walls and a central longitudinal bore tapered inwardly from one end to the other whereby the side wall of the tubular nozzle of the cement injection means will frictionally engage the tapered bore when said nozzle is pressed therein to form a pressure sealing relation therewith.

8. Apparatus for sealing the opening of a bone cavity according to claim 1 in which said expansible pressure sealing means comprises a generally rectangular member formed of elastomeric material and having a generally rectangular portion configured to be frictionally and removably received partially within a femoral canal in a relaxed condition for providing a pressure seal within the opening of a femoral cavity in an expanded condition, a central longitudinal aperture extending therethrough, and a peripheral flanged portion surrounding the rectangular portion at one end thereof to sealingly engage the exterior plateau surface surrounding the opening of the femoral cavity, said expander means comprises a generally rectangular wedge-shaped member formed of rigid material having tapered side walls configured to be frictionally received within the central longitudinal aperture of said sealing means whereby the side walls of said sealing means will be forced radially outward to seal the opening of the femoral cavity as said expanding means is pressed into said sealing means longitudinal aperture, and said expander means having a central longitudinal bore tapered inwardly from one end to the other whereby the side wall of the tubular nozzle of the cement injection means will frictionally engage the tapered bore when said nozzle is pressed therein to form a pressure sealing relation therewith, said expander means and said pressure sealing means in the expanded condition providing a pressure seal between the bone cavity opening and the injecting means whereby the penetrating bone cement will be injected into the bone cavity under substantial pressure and will penetrate between the trabeculae of the bone to thereby provide a bone/cement interface to securely hold said prosthetic device in place.

9. A method of sealing the opening of a femur bone cavity during injection of penetrating bone cement into the bone cavity under sufficient pressure to cause the cement to penetrate between the trabeculae of the bone prior to placement of a prosthetic device into the bone cavity, said method comprising the steps of;

removing the head of the femur to leave an irregular shaped, generally oval opening at the top end of the bone, reaming the interior of the femoral canal to create an elongate cavity, installing a plug at the lower end of the cavity in a manner to prevent bone cement from escaping thereby, filling the plugged femur cavity with penetrating bone cement from the plug to the lip of the opening of the femur, installing an expansible sealing plug having a longitudinal aperture extending therethrough partially into the opening such the one portion is inside the cavity and another portion is outside the cavity, installing a tapered expander member having a tapered bore extending therethrough in communication with the cavity into the aperture of the sealing plug such that the plug is expanded radially outward to conform to the shape of the opening and form a sealing engagement therewith and the portion of the plug inside the cavity is expanded to seal against the inside walls of the cavity adjacent the opening and portion outside the cavity engaging the exterior plateau surface surrounding the opening in a sealing relation, inserting the tubular nozzle of a cement cartridge carried in a cement injection gun into the tapered bore with sufficient force to become frictionally engaged on the bore side wall, creating pressure within the cement mass by pressing the cement injection gun against the assembled sealing plug and expander member and squeezing the handle and trigger of the gun together thereby causing the injection gun to develop high pressure within the cement mass for a predetermined time period, said expander member and said sealing plug in the expanded condition providing a pressure seal between the bone cavity opening and the injection gun whereby the penetrating bone cement will be injected into the bone cavity under substantial pressure and will penetrate between the trabeculae of the bone, and following the predetermined time period of cement pressurization, inserting the stem of a prosthesis into the cement and allowing the cement to harden to provide a bone/cement interface to securely hold the prosthetic device in place.

* * * * *